US012727921B2

(12) United States Patent
Legallois

(10) Patent No.: US 12,727,921 B2
(45) Date of Patent: Sep. 8, 2026

(54) DEVICE FOR FIXING A BONY STRUCTURE TO A SUPPORT MEMBER

(71) Applicant: Zimmer Spine, Bordeaux (FR)

(72) Inventor: Georges Legallois, Bordeaux (FR)

(73) Assignee: LDR MEDICAL, S.A.S., Sainte-Savine (FR)

( * ) Notice: Subject to any disclaimer, the term of this patent is extended or adjusted under 35 U.S.C. 154(b) by 453 days.

(21) Appl. No.: 17/967,105

(22) Filed: Oct. 17, 2022

(65) Prior Publication Data

US 2023/0042765 A1 Feb. 9, 2023

Related U.S. Application Data

(60) Continuation of application No. 16/698,455, filed on Nov. 27, 2019, now Pat. No. 11,497,531, which is a continuation of application No. 15/873,599, filed on Jan. 17, 2018, now Pat. No. 10,499,953, which is a division of application No. 14/805,281, filed on Jul. 21, 2015, now Pat. No. 9,901,377, which is a continuation of application No. PCT/EP2014/051744, filed on Jan. 29, 2014.

(30) Foreign Application Priority Data

Jan. 31, 2013 (EP) .................................... 13305107

(51) Int. Cl.
*A61B 17/70* (2006.01)
*A61B 90/00* (2016.01)

(52) U.S. Cl.
CPC ........ *A61B 17/7029* (2013.01); *A61B 17/705* (2013.01); *A61B 17/7053* (2013.01); *A61B 17/707* (2013.01); *A61B 2090/037* (2016.02)

(58) Field of Classification Search
None
See application file for complete search history.

(56) References Cited

U.S. PATENT DOCUMENTS 8,936,625 B2 1/2015 Larroque-Lahitette et al.
9,642,719 B1 * 5/2017 Aslie .................... A61F 2/4455
9,668,774 B2 6/2017 Larroque-Lahitette
(Continued)

FOREIGN PATENT DOCUMENTS

EP 2052689 4/2009
EP 2762095 5/2016
(Continued)

OTHER PUBLICATIONS

Official Action for U.S. Appl. No. 14/805,281, dated Dec. 1, 2016 5 pages, Restriction Requirement.
(Continued)

*Primary Examiner* — Jan Christopher L Merene

(57) ABSTRACT

Device for fixing a bony structure to a support member, the device comprising a first connecting member which comprises: a main body provided with a first passage configured for receiving the support member, and with a first opening configured for passing a flexible member therethrough; and a rod fixed to and/or monobloc with the main body and protruding therefrom. The device further comprises a first flexible member passing through the first opening of the main body and extending beyond the main body for attachment to the bony structure.

19 Claims, 5 Drawing Sheets

(56) References Cited

U.S. PATENT DOCUMENTS

| | | | | |
|---|---|---|---|---|
| 9,901,377 | B2 | 2/2018 | Legallois | |
| 10,499,953 | B2 | 12/2019 | Legallois | |
| 11,497,531 | B2 | 11/2022 | Legallois | |
| 2008/0058818 | A1* | 3/2008 | Schwab | A61B 17/7032 606/328 |
| 2009/0105715 | A1 | 4/2009 | Belliard et al. | |
| 2010/0249845 | A1 | 9/2010 | Meunier et al. | |
| 2011/0040328 | A1 | 2/2011 | Miller et al. | |
| 2011/0087287 | A1 | 4/2011 | Reeder, Jr. et al. | |
| 2011/0137345 | A1 | 6/2011 | Stoll et al. | |
| 2011/0245875 | A1* | 10/2011 | Karim | A61B 17/7037 606/264 |
| 2011/0257686 | A1* | 10/2011 | Metcalf, Jr. | A61B 17/7001 606/264 |
| 2011/0270314 | A1 | 11/2011 | Mueller et al. | |
| 2011/0301644 | A1* | 12/2011 | Belliard | A61B 17/702 606/264 |
| 2012/0130373 | A1 | 5/2012 | Larroque-Lahitette | |
| 2013/0023878 | A1* | 1/2013 | Belliard | A61B 17/7053 606/74 |

FOREIGN PATENT DOCUMENTS

| | | |
|---|---|---|
| FR | 2749155 | 12/1997 |
| WO | WO 2004/010881 | 2/2004 |
| WO | WO 2007/036657 | 4/2004 |
| WO | WO 2010/043496 | 4/2010 |
| WO | WO 2011/012690 | 2/2011 |
| WO | WO 2011/083261 | 7/2011 |
| WO | WO 2012/025585 | 3/2012 |
| WO | WO 2013/001180 | 1/2013 |
| WO | WO 2014/118250 | 8/2014 |

OTHER PUBLICATIONS

Official Action for U.S. Appl. No. 14/805,281, dated Mar. 14, 2017 9 pages, Replacement Of Dec. 1, 2016 Restriction Requirement.

Official Action for U.S. Appl. No. 14/805,281, dated Jun. 13, 2017 10 pages.

Notice of Allowance for U.S. Appl. No. 14/805,281, dated Oct. 18, 2017 7 pages.

U.S. Appl. No. 14/805,281, Response filed Jan. 18, 2017 to Restriction Requirement mailed Dec. 1, 2016, 8 pgs.

U.S. Appl. No. 14/805,281, Response filed Apr. 27, 2017 to Restriction Requirement mailed Mar. 14, 2017, 8 pages.

U.S. Appl. No. 14/805,281, Response filed Sep. 7, 2017 to Non-Final Office Action mailed Jun. 13, 2017, 15 pages.

U.S. Appl. No. 15/873,599, Non Final Office Action mailed Apr. 11, 2019, 16 pages.

U.S. Appl. No. 15/873,599, Notice of Allowance mailed Aug. 7, 2019, 5 pages.

U.S. Appl. No. 15/873,599, Preliminary Amendment Filed Mar. 21, 2018, 7 pages.

U.S. Appl. No. 15/873,599, Response filed Jul. 8, 2019 to Non Final Office Action mailed Apr. 11, 2019, 14 pages.

U.S. Appl. No. 15/873,599, Examiner Interview Summary mailed Jul. 8, 2019, 4 pages.

International Application Serial No. PCT/EP2014/051744, International Preliminary Report on Patentability mailed Aug. 13, 2015, 9 pages.

International Application Serial No. PCT/EP2014/051744, International Search Report mailed Mar. 12, 2014, 5 pages.

International Application Serial No. PCT/EP2014/051744, Written Opinion mailed Mar. 12, 2014, 7 pages.

European Application Serial No. 13305107.8, Decision to Grant mailed Apr. 29, 2016, 2 pages.

European Application Serial No. 13305107.8, Examination Notification Art. 94(3) mailed May 27, 2015, 7 pages.

European Application Serial No. 13305107.8, Extended European Search Report mailed Oct. 18, 2013, 8 pages.

European Application Serial No. 13305107.8, Office Action mailed Dec. 7, 2015, 32 pages.

* cited by examiner

X
3
22
2J
9
2
15
50
12J
13
14

A
33
G1
19
21
D1
1J
11J
X
20E
20E
6A
6
2
2J
1
50
1J
5
6B 20
20P

DEVICE FOR FIXING A BONY STRUCTURE TO A SUPPORT MEMBER

CROSS REFERENCE TO RELATED APPLICATIONS

This application is a continuation of U.S. patent application Ser. No. 16/698,455, filed Nov. 27, 2019, now U.S. Pat. No. 11,497,531, which is a continuation of U.S. patent application Ser. No. 15/873,599, filed Jan. 17, 2018, now U.S. Pat. No. 10,499,953, which is a divisional of U.S. patent application Ser. No. 14/805,281, filed Jul. 21, 2015, issued as U.S. Pat. No. 9,901,377, which is a continuation of PCT International Application No. PCT/EP2014/051744, filed Jan. 29, 2014; which claims priority to European Patent Application No. 13305107.8, filed Jan. 31, 2013, the contents of which are fully incorporated herein by reference.

TECHNICAL FIELD

The present disclosure generally relates to a device for fixing a bony structure to a support member, to a system comprising such a device and to a method using it.

One field of application for the device is holding together a bony structure and a support member in a desired relative position, for example to aid in healing of breaks or to correct bony structure deficiencies and abnormalities. In particular, the device may be helpful for holding a spinal structure (such as a set of vertebrae or a single vertebra) and a support member (such as a rod) in a desired configuration, to correct abnormal spine curvature or other spine deficiencies.

More particularly, the present disclosure relates to a system and method for stabilizing vertebrae.

BACKGROUND

The spine is formed of superposed vertebrae, normally aligned along a vertebral axis, from the lumbar vertebrae to the cervical vertebrae, each having an anterior part called the vertebral body, and a posterior part called the vertebral arch, or neural arch, the anterior and posterior parts enclosing the vertebral foramen. Each vertebral arch is formed by a pair of pedicles and a pair of laminae, with transverse processes and/or a spinous process (or neural spine) projecting therefrom. The transverse processes and the spinous process project opposite to the vertebral foramen.

When the vertebrae are articulated with each other, the vertebral bodies form a strong pillar for the support of the head and trunk. In between every pair of vertebral bodies, there is an intervertebral disc.

When the spine of a person has abnormal curvature (e.g. scoliosis) or other deficiencies (e.g. a damaged intervertebral disc), the vertebrae are typically too close together, too far apart or otherwise misaligned, and there is a need to stabilize the vertebrae in a correct position relative to one another. Mainly, there is either a need to compress the vertebrae, i.e. to bring and hold them closer together, or a need to distract the vertebrae, i.e. to move and keep them away from each other.

Devices known in the art for holding vertebrae relative to one another typically include one or more support members such as rods that are attached to the vertebrae by means of pedicle screws, hooks, or flexible ligatures.

Pedicle screws typically have a tulip-shaped head to which the rod is attached. Examples of a pedicle screw are given in patent document US2011/0040328A1. Pedicle screws are screwed into the pedicles of the vertebrae for forming fixing points on the vertebrae. However, in some cases the pedicles are small and/or deteriorated, e.g. due to osteoporosis, can be damaged or, more generally, do not provide sufficient purchase to hold the screw through time.

Patent document EP2052689A1 discloses examples of devices using a flexible ligature. In such devices, a connection member, or connector, is fixed to the rod and a flexible elongate ligature connects the connector to at least one rib and/or transverse process and/or lamina, the connector maintaining traction applied to the ligature. However, ligature attachment sometimes allows a certain amount of relative movement between the connector and the vertebra, which can be a drawback in some cases.

Patent document WO2012/025585 discloses a device using both a hook and a flexible ligature to connect a support member to one location in a bony structure.

While known devices have proven effective, further improvements would be beneficial.

SUMMARY

Described is a fixing device for fixing a bony structure to a support member, the fixing device comprising:

a first connecting member which comprises:

a main body provided with a first passage configured for receiving the support member, and with a first opening configured for passing a flexible member therethrough, and a rod fixed to and/or monobloc with the main body and protruding therefrom, the fixing device further comprising a first flexible member passing through the first opening of main body and extending outside, or beyond, the main body for attachment to the bony structure.

The main body may be of a type as disclosed, for instance, in patent documents WO2004/010881, WO2007/036657, WO2011/012690, WO2011/083261 or WO2013/001180. The first passage passes through the main body in a first direction.

The rod may be fixed to the main body by welding, friction or any other suitable fixing technique, for instance. Alternatively or concomitantly, the rod may be monobloc with the main body, i.e. it may be integrally or monolithically made with the main body. The free end of the rod (i.e. the end opposite to the main body) may be ball-shaped and, thus, configured to be received within a female ball-shaped socket. An example of ball-shaped socket is disclosed, for instance, in patent document WO2010/043496. The rod may extend in a second direction substantially parallel to and laterally offset from the first direction.

The flexible member may be, for instance, a band, a wire, a ligament, a strand, or a cord. The flexible member may be made of any suitable material which enables the fabrication of such a flexible member. For instance, it may be made of a metal, a polymeric material or a combination thereof.

In certain embodiments, the fixing device comprises a bone anchor having a bone anchoring part for fixation to the bony structure, and a connection head adapted for connecting the rod to the bone anchor. The bone anchoring part may be a threaded shank or a hook. The connection head may comprise a receiver for receiving the rod and a compression member engageable with the receiver for clamping the rod in the receiver. The bone anchor may thus essentially be a well-known pedicle screw as cited above or a hook with a connection head.

The bone anchor may provide a rigid and strong connection to the bony structure and prevent any fatigue phenomena in the connection over time, while the flexible member may improve the stability of the bone anchor on the bony structure. In particular, when the bone anchor is a hook, the risk that the hook may disengage from the bony structure is reduced by the anchorage provided by the flexible member. So, while the flexible member may provide a reliable fixation to the bony structure, the bone anchor may support the flexible member upon transient loads and restrict movement allowed by the possible elastic properties of the flexible member. The connection to the bony structure is, therefore, more reliable.

In other embodiments, the fixing device comprises a second connecting member similar to the first one and configured for receiving said support member, and a connection sleeve adapted for securing together the rods of the first and second connecting members. Thus, the sleeve provides additional connection between the first and second members which are already connected via the support member.

Such a fixing device may be used in a number of different ways, and provide various advantages depending on the way it is used. Examples of use and their associated advantages are detailed below.

In certain embodiments, the flexible member passes through the first passage, between the support member and the main body, in particular, the main body may be provided with a second passage communicating with the first passage, and configured to guide the flexible member therethrough.

In certain embodiments, the fixing device comprises at least one clamping mechanism for clamping the support member and/or the flexible member. The clamping mechanism may be engageable with the main body for clamping the support member and/or the flexible member to the main body. In particular, the support member may be clamped in the first passage. The clamping mechanism and the main body may be adapted for clamping simultaneously the support member and the flexible member to the main body. More particularly, the flexible member may be clamped between the support member and the main body while the support member is clamped within the main body.

A variety of clamping mechanisms that cause the flexible member and support member to remain in a fixed position relative to the main body can be used. For example, two or more separate clamping mechanisms may be used to hold the flexible member and support member in a fixed position individually, or a single clamping mechanism may be used for both the flexible member and support member. In addition, when two portions of the flexible member need to be fixed, they may be fixed simultaneously by the same clamping mechanism, or individually by separate clamping mechanisms.

Likewise, the flexible member may comprise two free ends forming a loop between them when being passed through the main body. Alternatively, as disclosed for instance in patent document WO2004/010881, a first end of the flexible member may be attached to the connecting member while a second end of the flexible member, which forms a free end, may be passed through the main body thus defining a loop between the first and second ends.

In certain embodiments, the first passage passes through the main body in a first direction and the rod extends in a second direction, offset relative to the first direction. The second direction may be substantially parallel to the first direction. Alternatively, the rod or at least a portion thereof may form an angle with the first direction.

In certain embodiments, the main body comprises first and second members defining between them the first passage, the second member being pivotable with respect to the first member, around a first axis. The rod may extend substantially along the first axis or substantially parallel to the first axis. The clamping mechanism may be engageable with the main body to move the first and second members towards each other for clamping the support member therebetween. Such an embodiment, where the main body resembles a pair of forceps or jaws, enables grapping the support member laterally. For instance, the main body may grasp a rod constituting the support member from the side without being axially pushed over the support member. Thus, the device may be readily added to already implanted systems or may be added at a stage of the surgery when the support member is, for instance, already inserted and primarily fixed by pedicle screws of lamina hooks. In any case, the connection of the main body to a support member is largely facilitated.

The clamping mechanism may be threadably engageable with the main body. The clamping mechanism may comprise a screw extending through an orifice provided in one of the first and second members and being received in a threaded hole provided in the other one of the first and second members, the screw being located opposite to the first axis with respect to the first passage. In particular, the clamping mechanism may be a screw with a screw head and a shank, the shank being rotatably engageable with the first member, and the screw head being configured to exert a force on the second member when the screw is tightened. Using a screw allows the physician (or other operative) to finely adjust the clamping force to the needs.

The fixing device may be adapted to clamp the flexible member between at least one of the first and second members and the support member disposed within the first passage. In this case, the flexible member and the support member can be simultaneously clamped, i.e. the flexible member and the support member can be simultaneously held in position relative to the main body.

At least one of the first and second members may be provided with at least one through opening forming the above-mentioned second passage. The through opening communicates with the first passage and guides the flexible member.

In certain embodiments, the clamping mechanism comprises a clamping member configured to cooperate with the first and second members so as to exert a force on the second member.

The present disclosure also relates to a connecting member for connecting a flexible member to a support member, as described hereinbefore.

Also described is a system for stabilizing a bony structure, e.g. a spinal structure, the system comprising:

- at least one support member,
- at least one fixing device with a connecting member and a flexible member as described above, for fixing the support member to the bony structure.

The system may further comprise at least one anchor having a bone anchoring part for fixation to the bony structure, and a connection head adapted for connecting the support member or the rod of the first connecting member to the anchor.

The support member may be rigid or not. Typically, the support member is a rod or equivalent. The support member may have various cross-sections and shapes.

Such a system may be used for stabilizing at least two vertebrae.

In certain embodiments, the system comprises at least two fixing devices having first and second connecting members, respectively, and two anchors for connecting the rods of the first and second connecting members to the bony structure.

In certain embodiments, the support member is U-shaped, thus defining two branches, and the first and second connecting members are adapted to receive the two branches, respectively.

In other embodiments, the system comprises at least two fixing devices having first and second connecting members, respectively, the first and second connecting members being adapted for receiving the support member. The system further comprises a connection sleeve adapted for securing together the rods of the first and second connecting members.

Also described is a method for fixing a bony structure to a support member, comprising the steps of:

- providing a support member,
- providing a first fixing device with a first connecting member and a first flexible member as described above,
- passing the first flexible member around the bony structure and tensioning the first flexible member, and
- impeding movement of the support member relative to the bony structure by fixing the position of the first flexible member and support member relative to the first connecting member.

This method may be used, in particular, for correcting abnormal spine curvature (e.g. scoliosis) or other spine deficiencies (e.g. a damaged intervertebral disc) by compressing or distracting vertebrae.

In certain embodiments, the method comprises the step of impeding movement of the first connecting member relative to the bony structure by fixing a bone anchoring part of a first bone anchor to the bony structure and connecting the rod of the first connecting member to the bone anchor. In such embodiments, the first flexible member and the first bone anchor may be fixed to different parts of the same vertebra. For instance, the flexible member may surround the lamina of the vertebra while the bone anchor may be fixed to the pedicle or the transverse process of the vertebra.

In certain embodiments, the method comprises the steps of: providing a second fixing device with a second connecting member and a second flexible member as described above; passing the second flexible member around the bony structure and tensioning the second flexible member; and impeding movement of the support member relative to the bony structure by fixing the position of the second flexible member and support member relative to the second connecting member. In addition, the first and second connecting members are secured together by means of a connection sleeve securing together their rods. In such embodiments, the first flexible member may be passed around a first vertebra of a spinal structure while the first flexible member may be passed around a second vertebra (distinct from the first one) of the spinal structure.

In certain embodiments, the method comprises the steps of: providing a second fixing device with a second connecting member and a second flexible member as described above; passing the second flexible member around the bony structure and tensioning the second flexible member; impeding movement of the support member relative to the bony structure by fixing the position of the second flexible member and support member relative to the second connecting member; and impeding movement of the second connecting member relative to the bony structure by fixing a bone anchoring part of a second bone anchor to the bony structure and connecting the rod of the second connecting member to the bone anchor. In such embodiments, the second flexible member and the second bone anchor may be fixed to different parts of the same vertebra. For instance, the flexible member may surround the lamina of the vertebra while the bone anchor may be fixed to the pedicle or the transverse process of the vertebra.

In certain embodiments, first and second fixing devices, first and second flexible members and first and second bone anchors are used, and the support member is U-shaped and defines two branches. These two branches are fixed to the first and second connecting members, respectively. In such embodiments, the first and second flexible members may be fixed, respectively, to lateral portions of a first vertebra, while the first and second bone anchors may be fixed respectively, to lateral portions of a second vertebra, distinct from the first one. The second vertebra may be adjacent to the first one. In particular, the first and second vertebrae may be the first and second cervical vertebrae called C1 and C2.

Other features and advantages of the invention will become apparent from the following detailed description, taken in conjunction with the accompanying drawings, which illustrate, by way of example, some principles of the invention.

BRIEF DESCRIPTION OF THE DRAWINGS

In the drawings, like reference signs generally refer to the same parts throughout the different views.

The drawings are not necessarily to scale, emphasis instead generally being placed upon illustrating the principles of the invention.

DETAILED DESCRIPTION

Figures 1, 2:
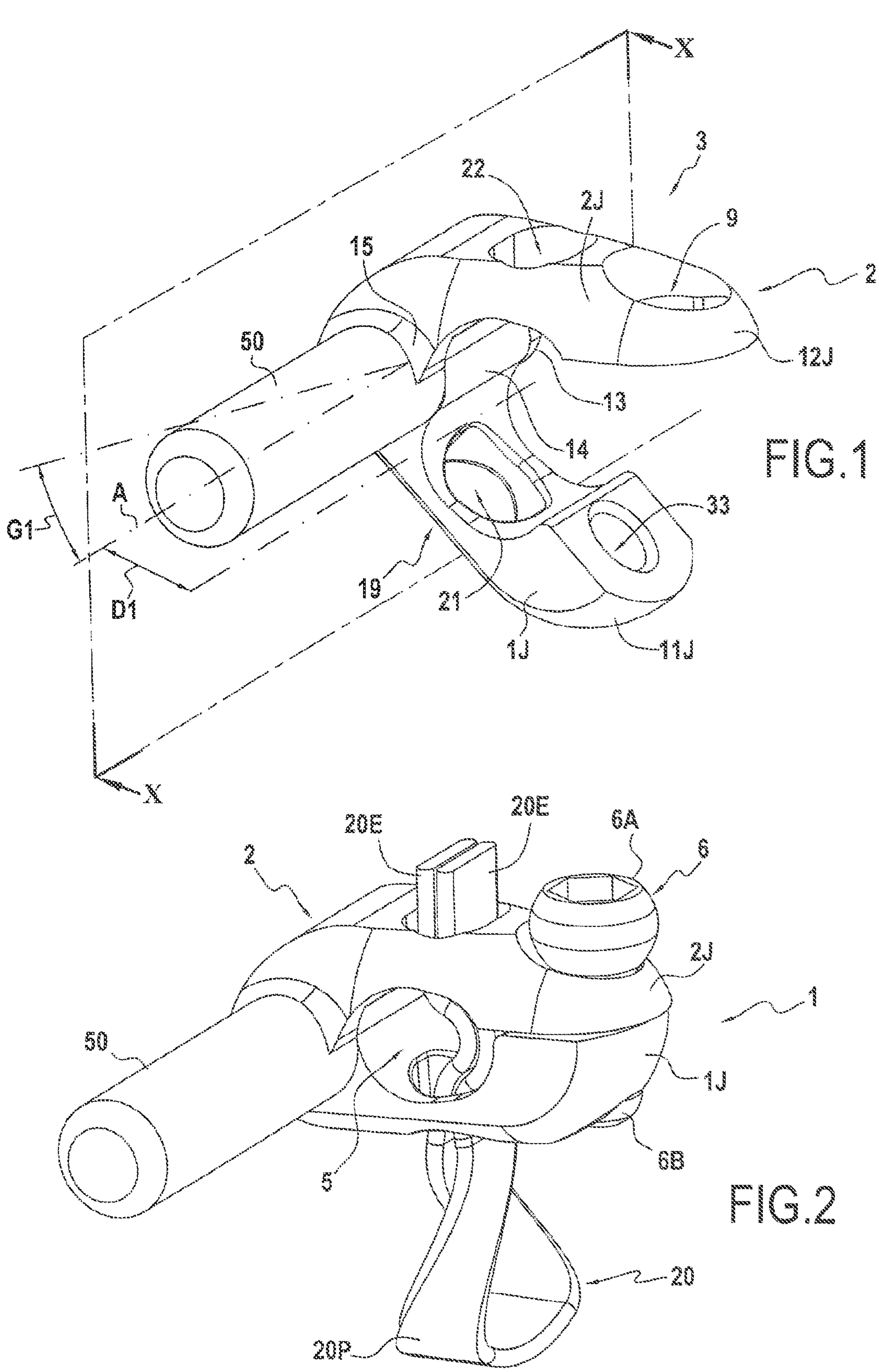
FIGS. 1 and 2 show an example of a fixing device.

In the following detailed description, it is referred to the accompanying drawings showing examples of fixing devices and stabilization systems. It is intended that these examples be considered as illustrative only, the scope of the invention not being limited to these examples.

To avoid details not necessary to enable those skilled in the art to practice the invention, the description may omit certain information known to those skilled in the art.

It is also noted that any reference to the words top, bottom, up and down, and the like, in the present disclosure refers to the orientation shown in the drawings, and is not intended to restrict the positioning of the device in actual use.

An example of fixing device 1 is shown in FIGS. 1 and 2. This device 1 is for fixing a support member 4 (see FIGS. 3-5) to a bony structure. The bony structure may be, for instance, a spinal structure comprising a set of vertebrae or only one vertebra.

In the illustrated example, the support member 4 is a rod. Here, the support member 4 is substantially straight, rigid and with a circular cross-section. However, it might have other rigidity, cross-section and/or shape. It may be made of biocompatible material, such as a metallic and/or polymeric material.

The fixing device 1 comprises a connecting member 3, shown in FIG. 1, which may be made of, for example, biocompatible metallic material. The connecting member 3 comprises a main body 2 forming a clamp. The main body 2 comprises a first member 1J and a second member 2J linked to the first member 1J over a hinge of axis A. In the figures, the first and second members 1J, 2J are, respectively, the lower and upper parts of the main body 2. In their closed position (see FIG. 2), the first and second members 1J, 2J define a first passage 5 between them. The support member 4, when positioned in the first passage 5, may extend substantially parallel to axis A.

The connecting member further comprises a shaft or rod 50 fixed to the main body 2 and protruding therefrom. The rod 50 may be integrally or monolithically made with the main body 2 and, in particular, with the first or second member 1J, 2J. In other instances, the rod 50 may be secured to the main body 2, e.g. the first or second member 1J, 2J, such as by welding. The rod 50 may protrude laterally from the main body 2, i.e. in a direction substantially perpendicular to the pulling direction applied to the flexible member 20 described hereafter. In the illustrated example, the rod 50 extends along the hinge axis A. However, the rod 50 may form an angle G1 with respect to the axis A and/or be offset relative to the axis A by a distance D1 in other embodiments.

The rod 50 may be of any appropriate shape. For instance, it may be cylindrical. The rod 50 may have a circular cross-section. It may have the same cross-section as that of the support member 4. In some instances, the rod 50 may include one or more flat surfaces, if desired.

Figure 10:
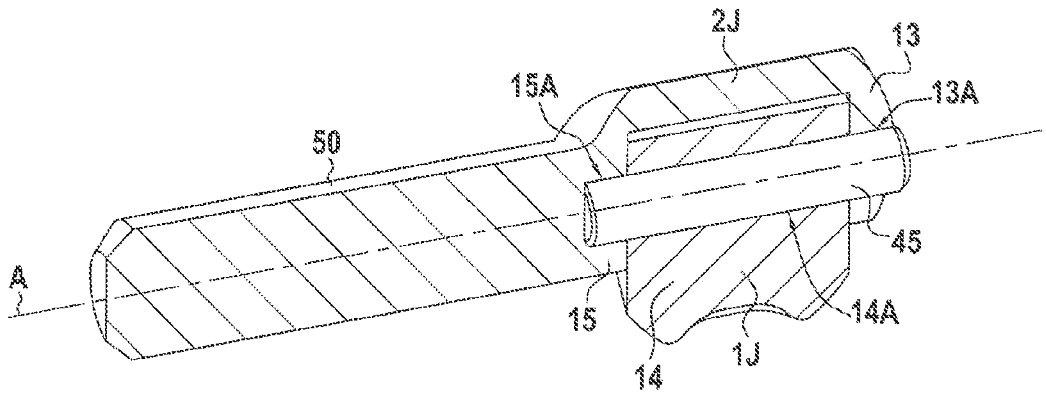
FIG. 10 is a cross-sectional view of the device of FIG. 1, along the plane X-X.

In instances in which the connecting member 3 is formed of multiple members, e.g. first and second members 1J, 2J, the first and second members 1J, 2J may be hingedly coupled together and pivot relative to each other about a pivot axis or hinge axis A. As illustrated in FIG. 10, the hinge may comprise a shaft or pin 45 passing thought the first and second members 1J. 2J. When the first and second members are assembled, the pin 45 may extend along axis A and go successively through a passage 13A provided in a first lateral leg 13 of the second member 2J, through a passage 14A provided in a central part 14 of the first member 1J, and through a passage 15A provided in a second lateral leg 15 of the second member 2J. The lateral legs 13, 15 of the second member 2J may be located on each side of the central part 14 of the first member 1J—see FIG. 1. The rod 50 may be integral or monolithically formed with the second lateral leg 15. In other instances the rod 50 may be welded, or otherwise fixed to the second lateral leg 15, for example. The passages 13A, 14A may be through holes. The passage 15A may be a blind hole. The passages 13A and 15A may have a circular cross-section of substantially the same size (i.e. substantially the same diameter) as that of the pin 45. When assembling the connecting member 3, the pin 45 may be held by friction, welding, swaging, crimping, pressing, clamping or any other appropriate fixing solution inside the openings 13A, 15A, or otherwise attached to the legs 13, 15 of the second member 2J. The pin 45 may be permitted to turn inside the opening 14A. Accordingly, the first member 1J may be movable in rotation (e.g. pivotable) around the hinge axis A, with respect to the second member 2J. In other instances, the first member 1J may include first and second lateral legs positioned on opposing sides of a central part of the second member 2J, for example, with a pin 45 hingedly coupling the first and second members 1J, 2J together, similar to that described above. In other embodiments, the pin 45 may be a unitary portion of one of the first and second members 1J, 2J.

The fixing device 1 further comprises a flexible member 20 (shown in FIG. 2, not depicted in FIG. 1) passing through the main body 2, e.g. through the first member 1J, through the first passage 5 between the members 1J, 2J, and through the second member 2J. The flexible member 20 extends from the main body 2 to form a loop 20P around a bony structure (not shown). Here, the flexible member 20 has two end portions 20E and an intermediate portion forming said loop 20P. The flexible member 20 may be configured such that the loop 20P extends outside the main body 2 from a passage or opening 21 provided in the first member 1J, and the end portions 20E extend from the main body 2 from a passage or opening 22 provided in the second member 2J—see FIGS. 1-2. The loop 20P may be tightened or tensioned around a bony structure by pulling on the end portions 20E, and the flexible member 20 may be locked in position by clamping the portions 1J, 2J and thus pressing the flexible member 20 between the support member 4 and a surface of the first and/or second member 1J, 2J.

In this example, there is only one exit opening 22 for the end portions 20E and one loop opening 21 for the loop 20P. However, in other examples, not shown, the main body 2 may be provided with two exit openings, i.e. one for each end 20E of the flexible member 20. Similarly, the main body 2 may be provided with two loop openings, i.e. one for each branch of the loop 20P. In other examples (not shown), the branches of the loop 20P may be separately locked in position relative to the main body 2, by distinct locking systems.

The main body 2 may be provided with a first passage 5 for receiving a portion of the support member 4. The first passage 5 may be defined by recesses provided in the inside faces of the first and second members 1J, 2J. The exit opening 22 and the loop opening 21 both communicate with the first passage 5. In the appended figures, the exit opening 22 is located above the first passage 5 whereas the loop opening 21 is located below the first passage 5. When the flexible member 20 is passed through the main body 2 and the support member 4 may be placed into the main body 2, between the members 1J, 2J, portions of the flexible member 20 (located between the end portions 20E and the loop 20P) may be held between the support member 4 and the inside faces of the members 1J, 2J defining the first passage 5. In the illustrated example, the exit opening 22, the first passage 5, and the loop opening 21 are substantially aligned and the flexible member 20 passes on the same side of the support member 4. In other examples, not shown, portions of the flexible member 20 may pass on each side of the support member 4. i.e. one branch of the flexible member 20 may pass on one side of the support member 4, while the other branch of the flexible member 20 may pass on the other side of the support member 4.

In other embodiments, the main body 2 may be a single member having a passage 5 extending therethrough for receiving the support member 4 therein. The openings 21, 22 for the flexible member 20 may communicate with the passage 5, such that the support member 4 may contact or press against portions of the flexible member 20 passing through the main body 2.

The fixing device 1 may also include a clamping mechanism to secure the support member 4 and/or the flexible member 20 to the main body 2. The support member 4 and the flexible member 20 may be simultaneously or separately secured to the main body 2. In some instances, a first clamping mechanism, e.g. a threaded fastener, may be used to clamp the support member 4 to the main body 2 and a second clamping mechanism, e.g. a threaded fastener, may be used to clamp the flexible member 20 to the main body 2, or a single clamping mechanism, e.g. a threaded fastener, may be used to simultaneously clamp the support member 4 and flexible member 20 to the main body 2. In the illustrative embodiment, the fixing device 1 comprises a clamping mechanism for bringing and maintaining the first and second members 1J, 2J in a clamping position in which the support member 4 and the flexible member 20 are held tight. Here, the support member 4 and the flexible member 20 are simultaneously clamped to the main body 2.

In the illustrated example, the clamping mechanism comprises a screw 6. The screw 6 has a shank 6B going through the first and second members 1J, 2J, and a head 6A having a profile (being internal or external) that allows the screw 6 to be driven in rotation. In more detail, the screw shank 6B may pass through an orifice 9 provided in an engagement portion 12J of the second member 2J, and can be screwed into a threaded hole 33 formed in an engagement portion 11J of the first member 1J. The screw shank 6B may be provided with an external thread for engagement with the internal thread of the hole 33.

The screw 6 and the engagement portions 11J, 12J of the first and second members 1J, 2J may be located on the side of the main body 2 which is opposite to the hinge (i.e. to the hinge axis A), with respect to the support member 4.

By tightening the screw 6, the first and second members 1J, 2J may be moved toward each other and the support member 4 may be clamped inside the first passage 5, between the first and second members 1J, 2J, while the flexible member 20 may be simultaneously clamped between the support member 4 and members 1J, 2J.

The screw head 6A may have a generally spherical, convex or conical shape and the lower part of the screw head (i.e. the part close to the shank 6B) may define a first sloped or curved surface. When the screw 6 is tightened, the screw head 6A may come into abutment with a second sloped or curved surface defined on the outside face of the engagement portion 12J, around the orifice 9, and the screw head 6A may push on the engagement portion 12J.

Figure 3:
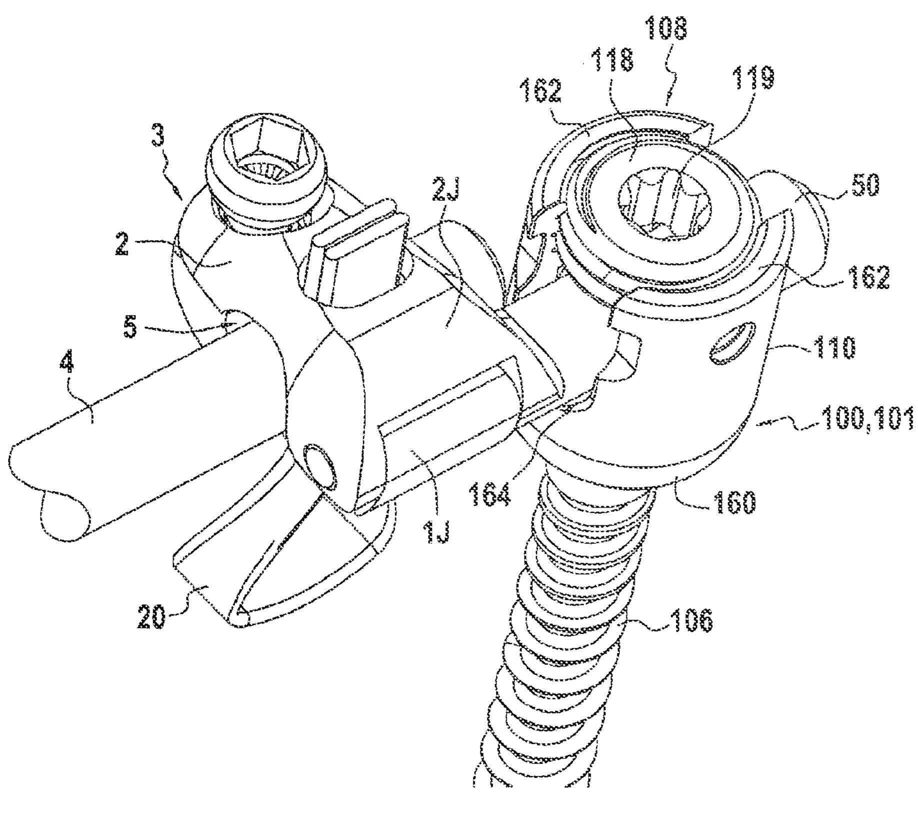
FIG. 3 shows the fixing device of FIG. 2 fitted with an example of a bone anchor, and connected to a support member.

In the example of FIG. 3, the fixing device 1 further comprises a bone anchor 100. Here, the bone anchor is a bone screw 101 and, more particularly, a pedicle screw. The screw 101 comprises a threaded shank 106 as an example of a bone anchoring part, and an upwardly extending upper portion, or connection head 108, being integral with the shank 106. The connection head 108 comprises a receiver 110 and a compression member 118.

The receiver 110 is generally U-shaped and defines a pair of opposed upstanding arms 162 integral with a base part 160 and forming a cradle and defining a slot or channel 164 between the arms 162, the channel 164 opening outwardly through the upper and lateral sides of the receiver 110. The channel 164 may have a width for snugly receiving the rod 50 of the connecting member 3 between the arms 162. Each of the arms 162 may have an interior surface that defines an internal passage and is provided with an internal thread configured to mate under rotation with an external thread provided on the compression member 118, so that the compression member 118 can be inserted and advanced downwardly into the channel 164, between the arms 162. The rod 50 may be laterally or downwardly loaded into the channel 164.

A tool engagement structure or inner drive 119 may be provided in the top surface of the compression member 118. The illustrated inner drive 119 is a multi-lobular cavity for engaging a driving tool (not shown) for screwing the compression member 118 into the receiver. When the compression member 118 is tightened, the compression member 118 pushes the rod 50 against the receiver 110, so as to fix the rod 50 relative to the whole screw 101.

When using such a fixing device 1, the flexible member 20 and the screw 101 may both be attached to a bony structure. The bony structure may be a vertebra. Then, typically, the screw 101 is anchored to the pedicle of the vertebra and the flexible member 20 is attached to the lamina. Thus, two different points of anchorage are provided, which improves the pulling resistance of the fixing device 1. This is particularly interesting when the pedicle is small and/or deteriorated, e.g. due to osteoporosis, and does not provide sufficient purchase to hold the pedicle screw 101 through time.

Figure 4:
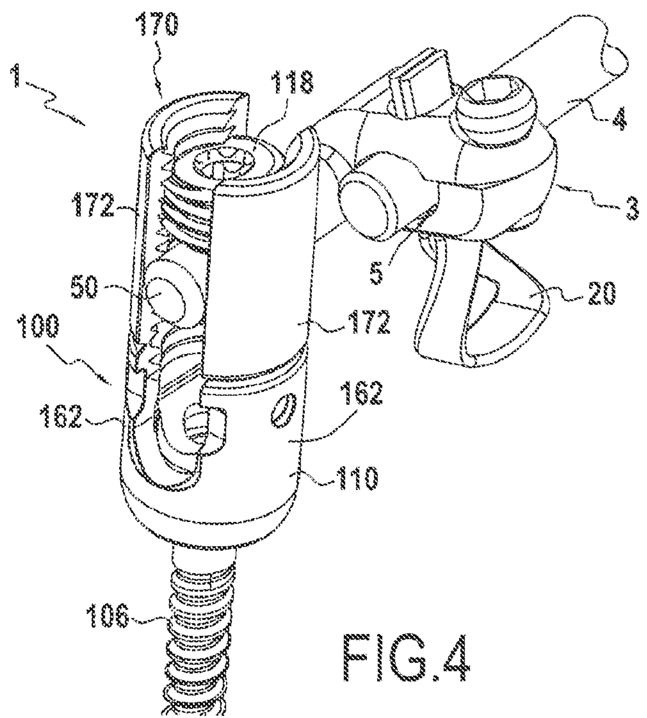
FIG. 4 shows the fixing device of FIG. 2 fitted with another example of a bone anchor, and connected to a support member.

FIG. 4 shows another example of fixing device 1. It differs from the example of FIG. 3 only by the fact that a sleeve 170 is detachably coupled to the receiver 110 of the screw 101. Such a screw is sometimes called a "long flange screw". In more detail, the sleeve 170 comprises two members or extensions 172 detachably coupled to and extending the receiver arms 162, respectively. Extensions 172 are provided with internal threads that match the internal threads of the arms 162 to form a continuous set of threads. Like the arms 162, extensions 172 are spaced from each other and define between them a gap in which the rod 50 can be inserted. When screwing the compression member 118 within the extensions 172, the compression member 118 pushes the rod 50 down to the base of the receiver 110. Such a configuration is particularly useful in a surgical spinal stabilization procedure called "reduction". During reduction, the support member 4 and the vertebra (not shown) are caused to move toward each other. The screw 101 may be anchored into the pedicle of a vertebra, and the flexible member 20 may be attached to the lamina of the vertebra. This makes the vertebra easier to handle and move relative to the support member 4 and, thus, improves the control and accuracy of the reduction.

Figure 5:
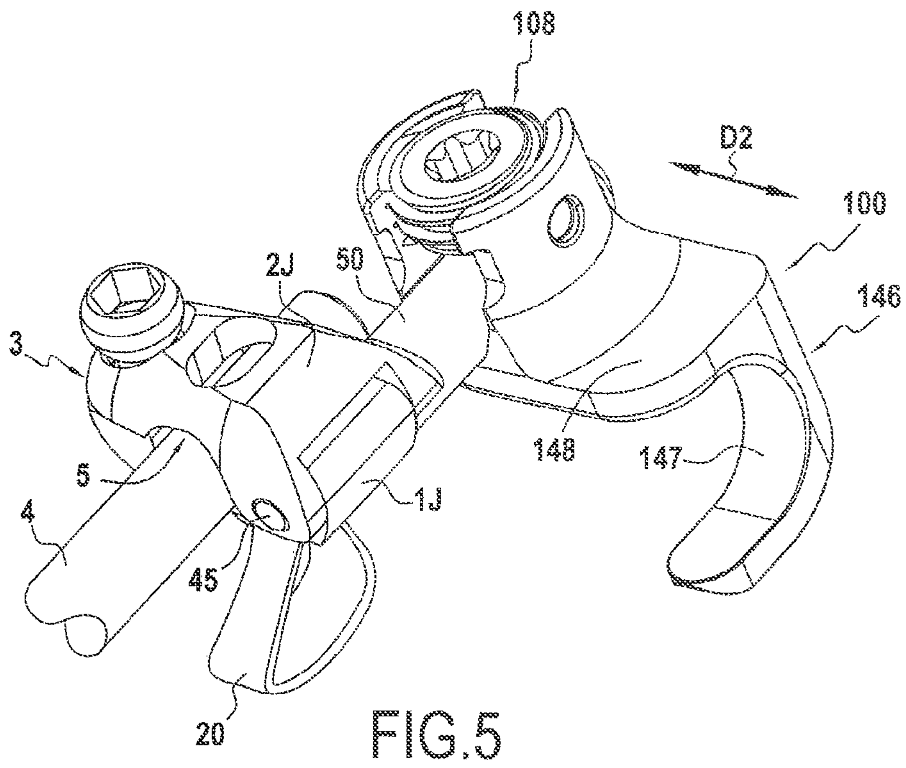
FIG. 5 shows the fixing device of FIG. 2 fitted with another example of a bone anchor, and connected to a support member.

FIG. 5 shows another example of fixing device 1. It differs from the example of FIG. 3 only by the fact that the threaded shank 106 of the bone anchor 100 is replaced by a hook 146. Here, the hook 146 has a distal hooking portion 147 configured for being hooked on the bony structure, a connection head 108 for receiving the rod 50 and an intermediate portion 148 between the head 108 and the hooking portion 147. The intermediate portion 148, which is optional, allows the hooking portion 147 to be offset relative to the rod 50 by a distance D2. This may render the positioning of the device easier. In particular, while the flexible member 20 is attached to the lamina of a vertebra, the hooking portion 147 may be anchored to the transverse process (instead of the pedicle) of the vertebra, which can be advantageous in certain situations and, in particular, may provide additional therapeutic options to the surgeon in certain situations.

With reference to FIGS. 3-5, it is to be noted that the rod 50 is offset relative to the first passage 5 of the connecting member 3 and, thus, relative to the support member 4, while the flexible member 20 is substantially in alignment with the first passage 5. This offset design is well adapted to certain situations and, in particular, when the support member 4 is to be implanted substantially along the lamina median plan of a spine. In such a case, the flexible member 20 may be attached to the lamina of a vertebra, while the bone anchor 100 may be attached to the pedicle or transverse process of the vertebra. Since, for anatomical reasons, the pedicle and transverse process of a vertebra are distant from the lamina of the vertebra, the offset design between the rod 50 and the support member 4 is advantageous.

It is also to be noted that the stable and strong fixation provided by the fixing device 1 is particularly advantageous when used for fixing an end of the support member 4 to a bony structure, as illustrated in FIGS. 3-5. Besides, the fixing device 1 being autostable, it allows the surgeon (or other operative) to independently fix the end of the support member 4 to the bony structure, if needed.

Figure 6:
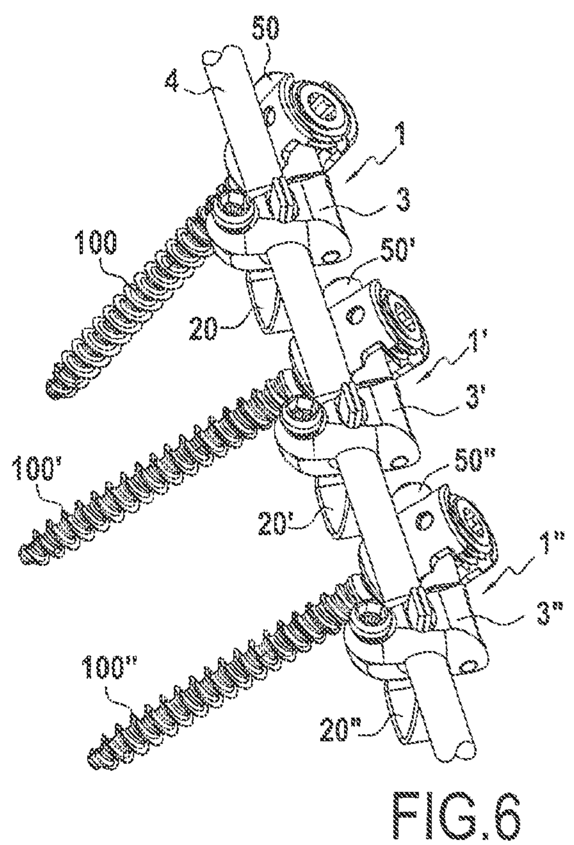
FIG. 6 shows an example of a stabilization system comprising fixing devices such as that of FIG. 2.

FIG. 6 shows an example of a stabilization system for stabilizing vertebrae (not shown), the system comprising: a first fixing device 1 configured to be fastened to a first vertebra, a second fixing device 1' configured to be fastened to a second vertebra, a third fixing device 1" configured to be fastened to a third vertebra, and a support member 4—e.g. a rod—for connecting the fixing devices together, thereby providing stabilization between the vertebrae. In this example, the fixing devices 1, 1', 1" are similar to that of FIG. 3. Each fixing device 1 may be fixed to a vertebra at two anchor points by means of its flexible member 20, 20', 20" and its bone anchor 100, 100', 100" (here a pedicle screw) respectively. As a result, the pulling resistance of the whole system is increased.

It is to be noted that, in particular situations, the fixing device of FIG. 6 may be used to strengthen the fixation of already existing, or "old", bone anchors 100, 100', 100" primarily fixed to a bony structure. In such situations, the old support member 4 primarily connected to the bone anchor may be removed therefrom and the rods 50, 50', 50" of the fixing device 1, 1', 1" may be connected to the old bone anchor 100, 100', 100", in place of the old support member 4. The old support member 4, or a new one, may then be clamped within the connecting members 3, 3', 3" of the fixing devices which are each attached to the bony structure via their flexible members 20, 20', 20". The flexible members 20, 20', 20" provide secondary anchor points to the bony structure, in addition to the primary anchor points provided by the old bone anchors 100, 100', 100". Thus, the pulling resistance of the whole system is increased.

Figures 7, 8:
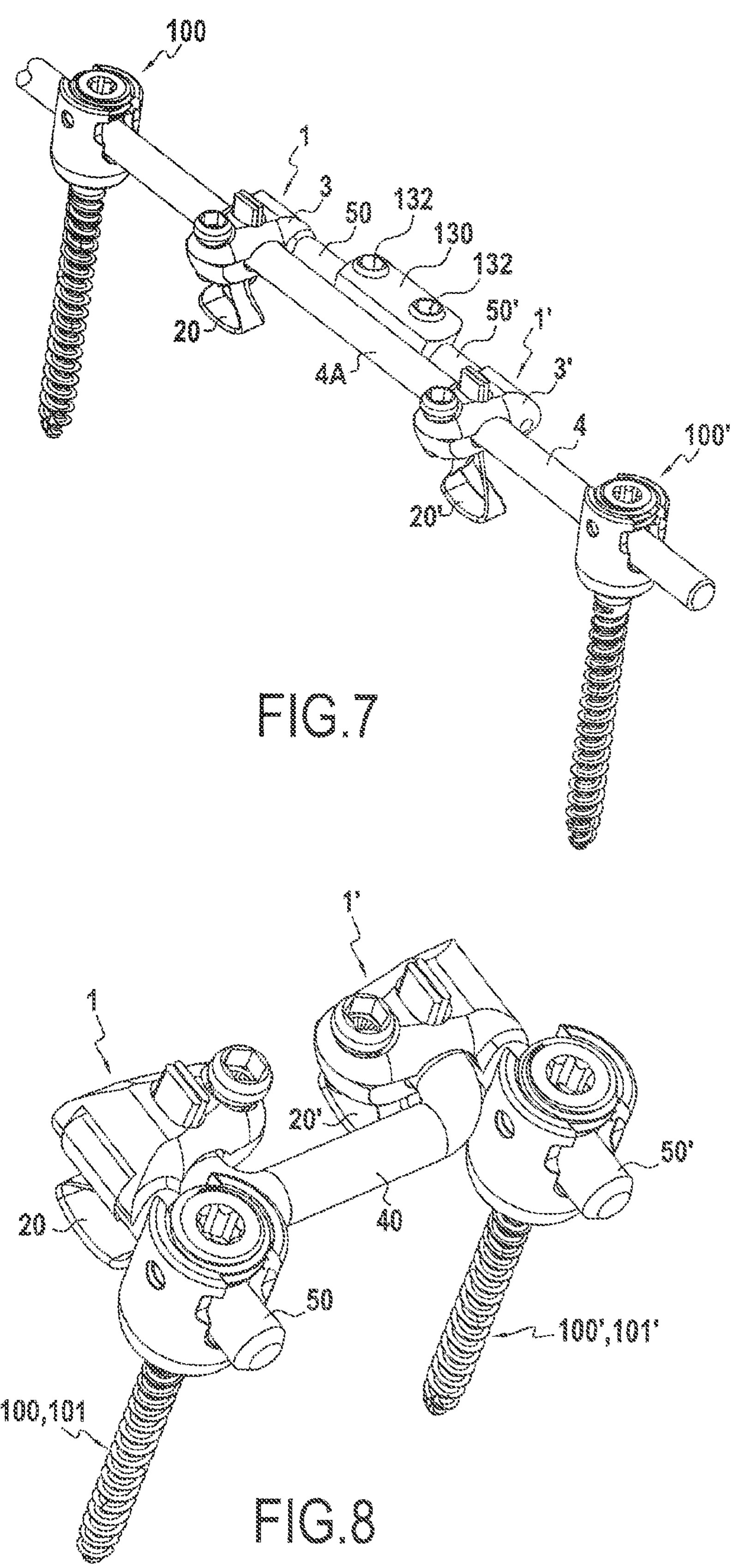
FIG. 7 shows another example of a stabilization system comprising fixing devices such as that of FIG. 2.
FIGS. 8 and 9 show another example of a stabilization system comprising fixing devices such as that of FIG. 2.

FIG. 7 shows another example of a stabilization system for stabilizing vertebrae (not shown), the system comprising: a first bone anchor 100 configured to be fastened to a first vertebra, a second bone anchor 100' configured to be fastened to a second vertebra, and a support member—e.g. a rod 4—for connecting the bone anchors 100, 100' together, thereby providing stabilization between the vertebrae. Here, the bone anchors 100, 100' are pedicle screws such as the one shown in FIG. 3 but those screws are used alone, their connection head receiving the support member 4. In this example, fixing devices 1 and 1' such as the one of FIGS. 1-2, comprising connecting members 3, 3', flexible members 20, 20', but no bone anchor, may be used to increase the stiffness of the support member 4, along a certain length thereof. To do so, the fixing devices 1 and 1' may be linked together by means of a connection sleeve 130. The connection sleeve 130 may define at least one internal through passage adapted for receiving the rods 50, 50' of the devices 1, 1'. In other instances, the connection sleeve 130 may define blind openings, recesses, or other passages for receiving the rods 50, 50'. The rods 50, 50' may be locked within the sleeve 130 by screws 132 protruding inside the internal passage when they are screwed down into the sleeve 130. Thus, the rods 50, 50' may be connected end-to-end via the connection sleeve 130. In other instances, the ends of the rods 50, 50' may be offset within the connection sleeve 130. Each of the fixing devices 1 and 1' may also be connected to a vertebra via its flexible member 20, 20', and to the support member 4 via its connecting members 3, 3'. As a result, at least the support-member portion 4A located between the fixing devices 1 and 1' may be stiffened due to the rods 50, 50' and to the anchor points provided by the flexible members 20, 20'.

Figure 9:
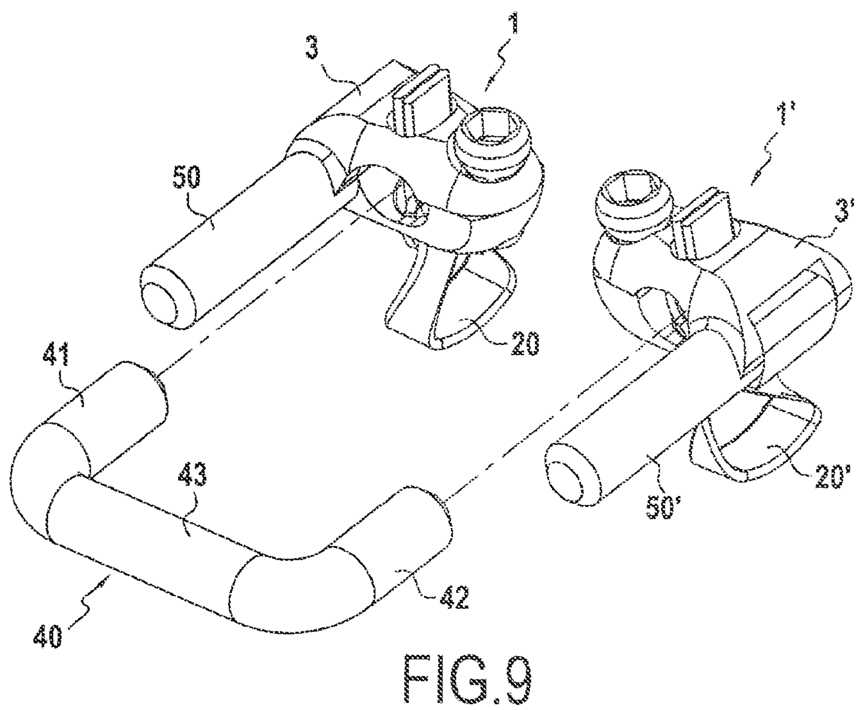

FIGS. 8 and 9 show another example of a stabilization system for stabilizing a bony structure. Such a system is particularly intended for stabilization of the C1-C2 segment of a spine, i.e. the spinal segment including the atlas (the cervical vertebra C1) and the axis (the cervical vertebra C2). The cervical vertebrae are the smallest vertebrae in the spine, reflective of the fact that they support the least load, and vertebra C1 is quite different from the other spinal vertebrae. Most notably it has no body or spinous process, but instead consists of a ring of bone made up of two lateral masses joined at the front and back by the anterior arch and the posterior arch. For these reasons, most of the stabilization systems are not well adapted to C1-C2 stabilization.

The system of FIGS. 8-9 comprises a first fixing device 1, a second fixing device 1' and a support member 40 for connecting the fixing devices 1, 1' together. In this example, the fixing devices 1, 1' are similar to the one of FIG. 3. Each fixing device 1, 1' comprises a connecting member 3, 3' with a rod 50, 50', a flexible member 20, 20' and a bone anchor 100, 100'. Here, the bone anchors 100, 100' are pedicle screws 101, 101'. The support member 40 may be U-shaped and define two branches 41, 42 joined together by a base 43. The two branches 41, 42 may be fixed to the first and second connecting members 3, 3', respectively, in the same way as the support member 4 is fixed to the connecting member 3 in FIG. 3.

Such a stabilization system may be used as follows. The flexible members 20, 20' are attached to the lateral masses of vertebra C1, respectively, while the bone anchors 100, 100', are anchored to the pedicles of vertebra C2, respectively (the size of the screws 101, 101' is adapted, to such a use, e.g. the pedicle screws 101, 101' are usually smaller than pedicle screws used for vertebrae other than vertebra C2). The rods 50, 50' may provide axial stiffness between vertebrae C1 and C2, and the support member 40 may provide torsional stiffness. As a result, the C1-C2 segment is stabilized.

The above description is given by way of example, and not limitation. Given the above disclosure, one skilled in the art could devise variations that are within the scope of the invention. Further, the features of the embodiments or examples disclosed herein can be used alone or in varying combinations with each other, and are not intended to be limited to the specific combination described herein.

What is claimed:

1. A method for preventing fatigue phenomena in a spinal structure, the method comprising:

implanting a first bone anchor at a first location of the spinal structure to provide a rigid bone connection;

attaching the first bone anchor to a rod extending from a first connecting member;

attaching a support member to the first connecting member such that the support member is generally parallel to the rod, wherein the first connecting member has a first passage extending therethrough configured to receive a first portion of the support member, and wherein the first passage is offset from the rod;

attaching a first flexible member to the first connecting member, wherein the first flexible member is attached to the spinal structure at a second location and extends through a pair of openings formed in the first connecting member, and wherein the pair of openings communicate with the first passage;

attaching a second flexible member at a third location of the spinal structure, wherein the second flexible member is attached to a second connecting member;

implanting a second bone anchor at a fourth location of the spinal structure, wherein the second bone anchor is attached to the support member via the second connecting member; and tensioning the first flexible member at the second location of the spinal structure to provide additional stability to the spinal structure.

2. The method of claim 1, wherein attaching the first flexible member to the first connecting member comprises clamping the first flexible member with a clamp of the first connecting member that is attached to the support member.

3. The method of claim 2, wherein tensioning the first flexible member the second location of the spinal structure comprises:

looping the first flexible member about the spinal structure at the second location;

pulling on end portions of the first flexible member; and tightening the clamp to secure the first flexible member in tension.

4. The method of claim 2, wherein attaching the support member to the first bone anchor via the first connecting member comprises attaching the first bone anchor proximate an end of the support member via the first connecting member.

5. The method of claim 2, wherein tensioning the first flexible member at the second location of the spinal structure comprises tensioning the first flexible member about an adjacent vertebra of a vertebra to which the first bone anchor is implanted.

6. The method of claim 5, further comprising not rigidly fixing the adjacent vertebra to the support member.

7. The method of claim 5, further comprising tensioning the second flexible member at the third location of the spinal structure to provide additional stability to the spinal structure, wherein the third location of the spinal structure to which the second flexible member is attached is different from the second location of the spinal structure to which the first flexible member is attached.

8. The method of claim 5, wherein the adjacent vertebra is located alongside the support member and is spaced from the first bone anchor.

9. The method of claim 5, further comprising:

elastically supporting the adjacent vertebra with the first flexible member; and supporting transient loads with the first bone anchor implanted in the vertebra.

10. The method of claim 1, wherein the first connecting member comprises first and second clamp members hingedly coupled together and configured to pivot relative to each other about a pivot axis.

11. The method of claim 10, wherein the rod extends along the pivot axis.

12. The method of claim 10, wherein attaching the support member to the first connecting member comprises driving a screw in rotation through an orifice formed in the first clamp member.

13. A system for supporting a spinal structure, the system comprising:

a rigid fixation system comprising:

a support member; and a first bone fastener configured to rigidly couple the support member to the spinal structure; and a first elastic fixation system comprising:

a first clamp mechanism including a first connecting member configured to attach to the support member via a support member passage formed through the first connecting member and configured to attach to the first bone fastener via a rod extending from the first connecting member and offset from the support member passage;

wherein when the support member is secured to the support member passage, the support member is generally parallel to the rod; and a first flexible member inserted through an opening in the first connecting member having a communication with the support member passage and configured to elastically couple the first connecting member of the first clamp mechanism to the spinal structure, wherein one or more of the following is true:

(a) the support member is coupled to the first bone fastener through the first clamp mechanism, and (b) the first clamp mechanism is configured to attach to an end of the support member.

14. The system for supporting a spinal structure of claim 13, wherein (a) is true.

15. The system for supporting a spinal structure of claim 13, wherein (b) is true.

16. The system for supporting a spinal structure of claim 13, wherein the first clamp mechanism is configured to position the first flexible member to couple to a first vertebra adjacent a second vertebra to which the first bone fastener is configured to couple.

17. The system for supporting a spinal structure of claim 16, wherein the first clamp mechanism is configured to clamp onto both the inserted first flexible member and the support member.

18. The system for supporting a spinal structure of claim 13, further comprising a second elastic fixation system comprising:

a second clamp mechanism including a second connecting member configured to attach to the support member of the rigid fixation system; and a second flexible member inserted into the second clamp mechanism and configured to elastically couple the second connecting member of the second clamp mechanism to the spinal structure.

19. The system of claim 13, wherein the first connecting member comprises a main body; and wherein the rod is integrally made with the main body.

* * * * *